(12) United States Patent
Romano

(10) Patent No.: US 6,862,940 B2
(45) Date of Patent: Mar. 8, 2005

(54) PORTABLE ELECTRO-HYDRAULIC TEST BED APPARATUS WITH ANALOG CONTROL STATION AND METHODOLOGY

(76) Inventor: Paul E. Romano, 136 E. Rosewood, San Antonio, TX (US) 78212

( * ) Notice: Subject to any disclaimer, the term of this patent is extended or adjusted under 35 U.S.C. 154(b) by 32 days.

(21) Appl. No.: 10/401,312

(22) Filed: Mar. 27, 2003

(65) Prior Publication Data

US 2004/0187597 A1 Sep. 30, 2004

(51) Int. Cl.[7] ................................................ G01N 3/02
(52) U.S. Cl. .............................. 73/856; 73/760; 73/168
(58) Field of Search ........................... 73/856–859, 168, 73/760, 37, 40, 40.5 R, 47

(56) References Cited

U.S. PATENT DOCUMENTS

| | | | |
|---|---|---|---|
| 3,151,478 A | * 10/1964 | Heldenbrand | ................ 73/49.2 |
| 3,577,768 A | * 5/1971 | Aprill et al. | .............. 73/40.5 R |
| 4,480,462 A | * 11/1984 | Miller | ............................ 73/37 |
| 5,079,707 A | 1/1992 | Bird et al. | |
| 5,115,407 A | 5/1992 | Bird et al. | |
| 5,198,980 A | 3/1993 | Patrick | |
| 6,349,601 B1 | * 2/2002 | Losee | ............................ 73/714 |

* cited by examiner

Primary Examiner—Edward Lefkowitz
Assistant Examiner—Alandra Ellington
(74) Attorney, Agent, or Firm—Michelle Evans; Gunn & Lee, P.C.

(57) ABSTRACT

A portable electro-hydraulic test bed apparatus with analog control station and methodology for performing hands-on materials and components testing. A portable test bench is provided having a hydraulic pump and a reservoir of hydraulic oil. The pressurized hydraulic fluid flows through a pressure relief valve, filter, and ball valve to a servo control valve. The servo control valve controls the action of the hydraulic ram. Any return hydraulic fluid flows through check valve, filter, and heat exchanger back to the reservoir. The servo control valve with the hydraulic ram may be moved to the location where the test is to occur. Whenever the hydraulic ram is moved to a different location displacement interlock is also required. The hydraulic ram is anchored at one end and the test is performed on the test item with the other end of the ram. A displacement sensor is included to determine how much the test item is being displaced. In addition, a load cell is included to determine the load that is exerted on the test item. A portable analog control station is provided.

16 Claims, 7 Drawing Sheets

PORTABLE ELECTRO-HYDRAULIC TEST BED APPARATUS WITH ANALOG CONTROL STATION AND METHODOLOGY

BACKGROUND OF THE INVENTION

1. Field of the Invention

Applicant's invention relates to a portable electro-hydraulic test bed apparatus with analog control station and methodology for performing hands-on materials and components testing.

2. Background Information

Engineering materials are commonly specified by their properties. Of all the properties a material may possess, mechanical properties are often the most important because virtually all fabrication processes and most service conditions involve some type of mechanical loading. Numerous products exist in the marketplace that are used to evaluate the mechanical and physical properties and performance of materials, structures and components. However, the majority of these products are large, cumbersome and lack cost effectiveness. A need therefore exists in the industry for an inexpensive and portable test bench that can perform a series of mechanical structure tests. Applicant has sought to satisfy this need with the present invention.

SUMMARY OF THE INVENTION

It is an object of the present invention to provide a novel portable electro-hydraulic test bed apparatus with analog control station and methodology for performing hands-on materials and components testing.

Still another object of the present invention is to provide a novel portable electro-hydraulic test bed apparatus which incorporates a hydraulic ram.

Another object of the present invention is to provide a novel portable electro-hydraulic test bed apparatus which incorporates an analog control system.

Still another object of the present invention is to provide a novel portable electro-hydraulic test bed apparatus wherein the control system is an analog closed loop control system which uses force or displacement as the feedback parameter.

Yet another object of the present invention is to provide a novel portable electro-hydraulic test bed apparatus which provides a displacement interlock control.

An additional object of the present invention is to provide a novel portable electro-hydraulic test bed apparatus which incorporates a hydraulic pump.

Still an additional object of the present invention is to provide a novel portable electro-hydraulic test bed apparatus which incorporates at least one oil filter.

Yet an additional object of the present invention is to provide a novel portable electro-hydraulic test bed apparatus which incorporates a valve control system.

Another object of the present invention is to provide a novel portable electro-hydraulic test bed apparatus which provides a portable test bench.

Still another object of the present invention is to provide a novel portable electro-hydraulic test bed apparatus which provides a pressure relief valve.

Another object of the present invention is to provide a novel portable electro-hydraulic test bed apparatus which provides a ball valve.

Still an additional object of the present invention is to provide a novel portable electro-hydraulic test bed apparatus which incorporates a servo control valve.

Yet an additional object of the present invention is to provide a novel portable electro-hydraulic test bed apparatus which incorporates a check valve.

Still another object of the present invention is to provide a novel portable electro-hydraulic test bed apparatus which incorporates a displacement sensor.

Another object of the present invention is to provide a novel portable electro-hydraulic test bed apparatus which provides at least one control card.

It is yet another object of the present invention to provide a novel portable electro-hydraulic test bed apparatus which incorporates a load/force sensor.

An additional object of the present invention is to provide a novel portable electro-hydraulic test bed apparatus which incorporates a hydraulic manifold.

Still another object of the present invention is to provide a novel portable electro-hydraulic test bed apparatus which provides a hydraulic pump motor.

It is another object of the present invention to provide a novel portable electro-hydraulic test bed apparatus which incorporates safety devices.

In satisfaction of these and related objectives, Applicant's present invention provides a portable electro-hydraulic test bed apparatus with analog control station and methodology for performing hands-on materials and components testing. A portable test bench is provided that has a hydraulic pump and a reservoir of hydraulic fluid. The pressurized hydraulic fluid flows through a pressure relief valve, filter, and ball valve to a servo control valve. The servo control valve controls the action of the hydraulic ram. Any return hydraulic fluid flows through check valve, filter, and heat exchanger back to the reservoir. The servo control valve with the hydraulic ram may be moved to the location where the test is to occur. Whenever the hydraulic ram is moved to a different location the need to include displacement interlock is required as well. The hydraulic ram is anchored at one end and the test is performed on the test item with the other end of the ram. A displacement sensor is included to determine how much the test item is being displaced during the test. In addition, a load cell is included to determine the load that is exerted on the test item.

The portable work bench can be located outside the item to be tested, but the hydraulic hoses and control cable would run into the test item. The hydraulic ram could be set inside the test item and the tests performed within the test item. The person performing the test can also have the control station for the apparatus adjacent him or her when watching the test from within the test item since the control station is on a tethered cable.

The control system of the present invention operates based on the manner in which the actuating signal is used to control the transfer of energy from source to load. The control system underlying the present invention is an analog closed loop control system. Essentially the control system operates on continuously varying data whereby any output force or displacement signal from the test item is fed back into the system for comparison with the initial resting state values and any interim testing values. The control system provides control to within an accuracy of 0.05% of the command in the elastic range of the article being tested. This type of control is advantageous over digital control since digital control only works in discrete units and is therefore referred to as discontinuous control. The control station of the present invention indicates to the test engineer system response values during the test and the continuous nature of the control system allows for precision control and adjustment instantly during a test. The system is capable of holding load and relieving load at the discretion of the engineer.

DETAILED DESCRIPTION OF THE PREFERRED EMBODIMENT

Figure 1:
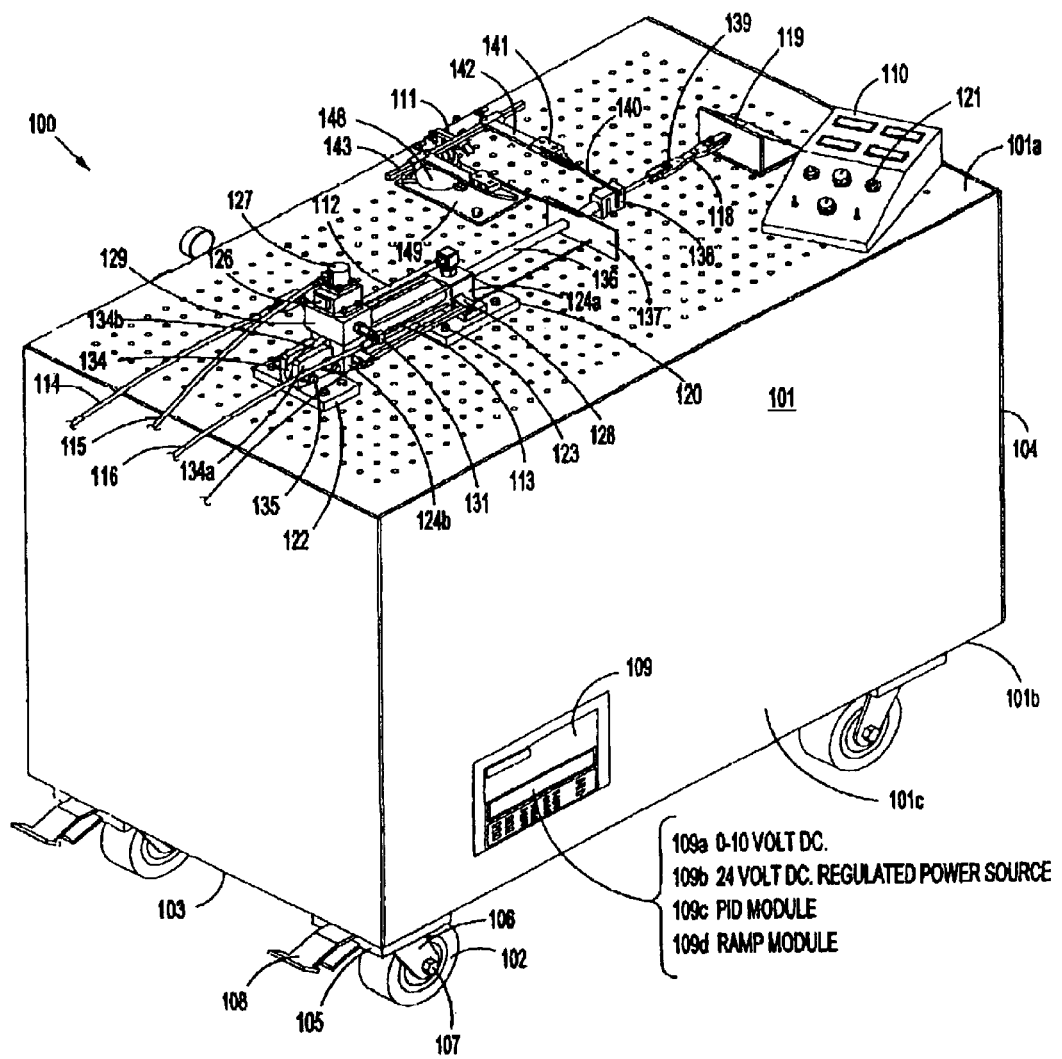
FIG. 1 is a perspective view of the preferred embodiment of the present invention.

FIG. 1 is a perspective view of the preferred embodiment of the present invention 100. A test bench 101 is provided being preferably rectangular in shape and having top 101a, bottom 101b and sides 101c. Test bench 101 is preferably supported from bottom 101b by a stabilizing number of wheels 102 near the front end 103 and rear end 104 of test bench 101. Wheels 102 are mounted to the bottom 101b by way of support brackets 105. Support brackets 105 connect to forks 106 on opposing sides of each wheel 102. Forks 106 connect to wheel 102 by way of hub 107. Wheels 102 are provided to give mobility to test bench 101. Locking means 108 is provided on at least two of the wheels 102 to lock test bench 101 in location before and after moving.

On the side 101c of test bench 101 is a control interface case 109. Control interface case 109 serves as the power interface for test bench 101. At control interface case 109, 0–10 volt DC fixed power source 109a is provided as well as a 24 volt DC regulated power source 109b. A proportional integral derivative (PID) module 109c is incorporated to regulate various process parameters such as pressure, total mass flow rate, phase volumetric fraction, phase mass flowrate, and pressure and liquid level. The regulation by the PID module 109c is accomplished by controlling outlet pressure, inlet total mass flowrate, valve opening and pump velocity. Control interface case 109 also provides a ramp module 109d. Ramp module 109d produces a DC output signal over an adjustable time rate setting based on the closure of an external contact. Ramp module 109d can have integral LED's indicating that its output is at minimum, or has reached a maximum output state. Ramp module 109d is useful for establishing the rate in which to achieve a predetermined tensile or compressive load/force measured by load/force cell 138 or a physical displacement of rod 136 measured by displacement transducer 113. The ramp rate is established by an adjustable rate knob located on control station 110. The preferred specifications for ramp module 109d are contained in Table 1.

TABLE 1

| Preferred Specifications of Ramp Module 109d. | |
| --- | --- |
| Power Supply | Regulated 18–26 VDC |
| Power Required | 4 VA |
| Command Signal | 0 to +10 VDC and 0 to −10 VDC |
| Ramp Disable Voltage | 5 to 30 VDC |
| Reference Outputs | +/− 10 VDC @10 ma |
| Output Voltage | 0 to +/− 10 VDC |
| Ambient Temperature Range | 32 F. to 158 F. standard |
| Ramp Time | Adjustable |

The control system underlying the present invention is an analog closed loop control system. In this arrangement, the control system operates on continuously varying data whereby any output force or displacement signal from the test item is fed back into the system for comparison with initial resting state values and any interim testing values. The control system provides control to within an accuracy of 0.05% of the command in the elastic range of the article being tested.

On top 101a of test bench 101 is control station 110, displacement interlock control 111, and hydraulic ram 112. Control station 110 maintains four display units for monitoring force feedback measured by load/force cell 138, displacement feedback measured by displacement transducer 113, command high setpoint and command low setpoint. Also maintained on control station 110 are analog controls with actuator knobs and switches 121 having the functions COMMAND SELECT (HIGH/ZERO/LOW), COMMAND HIGH SETPOINT, COMMAND LOW SETPOINT, RAMP ENABLE, RAMP RATE-SELECTABLE, CONTROL SELECT (FORCE OR DISPL) used in controlling the present invention. The control station 110 indicates to the test engineer system response values during the test and the continuous nature of the control system allows for precision control and adjustment instantly during a test. The control system through control station 110 is capable of holding load and relieving load at the discretion of the test engineer.

Figure 2:
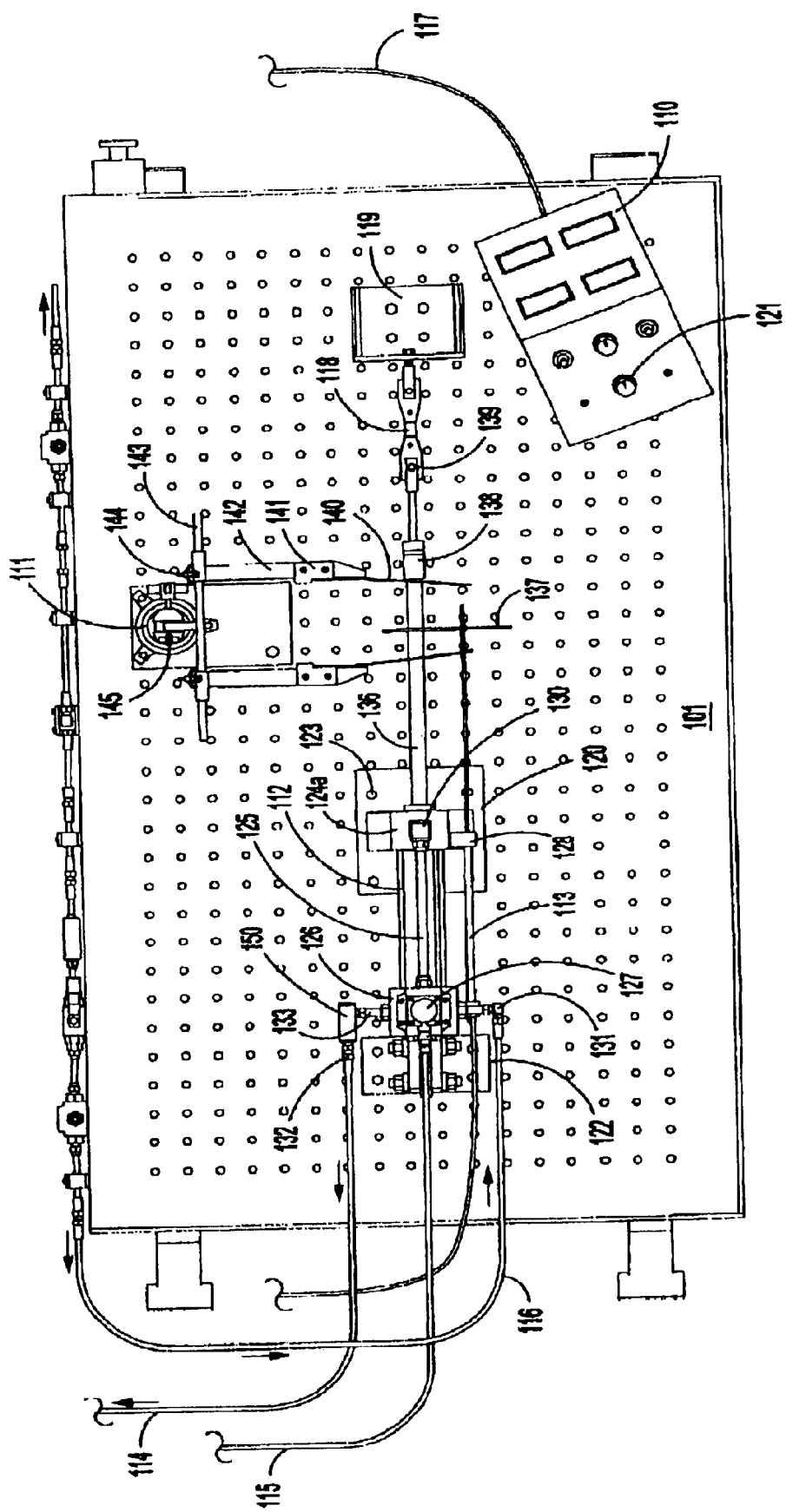
FIG. 2 is a top view of the preferred embodiment of the present invention.

Control station 110 is connected to test bench 101 through a tethered cable 117 (See FIG. 2). Hydraulic ram 112 is used for supplying tension or compression to the item being tested. Hydraulic ram 112 is a single-acting cylinder with a single diameter ram type plunger incorporating a "tie rod" design. The preferred specifications for the hydraulic ram 112 are contained in Table 2.

TABLE 2

Preferred Specifications for Hydraulic Ram 112.

| | |
|---|---|
| Nominal Pressure | 1000 psi dependent on bore size |
| Standard Temperature | −10 F. to +165 F. |
| Bore Size | 1 inch through 8 inches |
| Piston Rod Diameter | ½ inch through 5½ inches |

Hydraulic ram 112 is connected to the top of level plate 120 at one end of hydraulic ram 112 by way of hydraulic ram rod end cover 124a. The opposite end of hydraulic ram 112 is directly connected to test bench 101 by way of hydraulic ram head end cover 124b. Positioned on top of hydraulic ram head end cover 124b is hydraulic manifold 129. Pressure line 116 carries fluid from hydraulic pump 161 (See FIG. 3) to the hydraulic manifold 129 of hydraulic ram 112 by way of union 131. Return line 114 carries exhaust fluid from the hydraulic manifold 129 of hydraulic ram 112 back to the oil reserve 151 (See FIG. 3). On top of hydraulic manifold 129 is valve 126. Servo cable 115 is connected to valve 126 by way of coil (not shown) under housing 127. Servo cable 115 supplies a combined transmission of power and control to coil (not shown). Coil (not shown) drives valve 126 which directs fluid into hydraulic manifold 129. Level plate 120 may or may not be attached to top 101a of test bench 101 by way of screws 123.

Connected by way of displacement transducer mounts 128 at the side of hydraulic ram 112 is displacement transducer 113. Displacement transducer 113 is provided to measure hydraulic ram 112 stroke. Base mount 122 is located adjacent hydraulic ram head end cover 124b and connected to hydraulic ram head end cover 124b by way of mated arms 134. Mated arms 134 include two stationary arms 134a situated horizontally on top of base mount 122 and one movable arm 134b extending pivotally from hydraulic ram head end cover 124b. Stationary arms 134a and movable arm 134b are connected by way of screws 135.

Extending on the opposite side of hydraulic ram rod end cover 124a portion of the hydraulic ram 112 is rod 136. The opposite end of rod 136 connects to one face of plate 137. Adjacent the opposing face of plate 137 is load/force cell 138, being preferably an S-beam. Load/force cell 138 measures the load provided by hydraulic ram 112. On the opposite side of load/force cell 138 are two strain inducers 139 with a centrally connected test specimen 118. The strain inducer 139 induces strain into the test item 118 which can be measured preferably with a strain gauge (not shown). The applied force can be either positive (tensile) or negative (compressive). Connected at the opposite end of the second strain inducer 139 is reaction mount 119. Reaction mount 119 mounts to test bench 101.

Situated above plate 137 and load/force cell 138 are arms 140 of displacement interlock control 111. At the opposite end of arms 140 are interlocks 141. Interlocks 141 are provided to prevent or allow a movement or operation of one part, only when the other part is locked in a pre-determined position. Interlocks 141 are situated on bars 142 which end in a central member 143. Base member 148 anchors displacement interlock control 111 to test bench 101 by way of platform 149. Safety devices consisting of multi-directional displacement interlocks 141, an easily accessible hydraulic pressure ON/OFF master switch 159 and an adjustable pressure relief valve 153. These safety devices provide the test bench 101 means to prevent overloading of the sample test item 118 during normal operation. These safety devices are capable of relieving pressure upon actuation.

In FIG. 2 a top view of the preferred embodiment of the present invention is shown. On top of test bench 101 is control station 110, displacement interlock control 111, and hydraulic ram 112. Control station 110 contains actuator knobs 121 used in controlling the hydraulic ram 112 of the present invention. Control station 110 is connected to test bench 101 through a tethered cable 117. Hydraulic ram 112 is connected to the top of level plate 120 at one end of hydraulic ram 112 by way of hydraulic ram rod end cover 124a. On top of hydraulic ram rod end cover 124a is union 130 which provides a connection to tube 125. Pressure line 116 carries fluid from hydraulic pump 161 (See FIG. 3) to the hydraulic ram 112 by way of union 131. Return line 114 carries exhaust fluid from the hydraulic ram 112 back to the oil reserve 151 (See FIG. 3) by way of union 133, check valve 150, and union 132. Valve 126 is provided. Servo cable 115 is connected to valve 126 by way of coil (not shown) under housing 127. Servo cable 115 supplies a combined transmission of power and control to valve 126. Level plate 120 may or may not be attached to top 101a of test bench 101 by way of screws 123. Connected by way of displacement transducer mounts 128 at the side of hydraulic ram 112 is displacement transducer 113. Displacement transducer 113 is provided to measure hydraulic ram 112 stroke. Base mount 122 is provided.

Extending on the opposite side of hydraulic ram rod end cover 124a portion of the hydraulic ram 112 is rod 136. The opposite end of rod 136 connects to one face of plate 137. Adjacent the opposing face of plate 137 is load/force cell 138, preferably an S-beam. On the opposite side of load/force cell 138 are two strain inducers 139 with a centrally connected test specimen 118. Connected at the opposite end of the second strain inducer 139 is reaction mount 119. Reaction mount 119 mounts to test bench 101.

Situated above plate 137 and load/force cell 138 are arms 140 of displacement interlock control 111. At the opposite end of arms 140 are interlocks 141. Interlocks 141 are situated on bars 142 which end in a central member 143. A means 144 for adjusting bars 142 is provided. Located centrally on central member 143 is side member 145.

Figure 3:
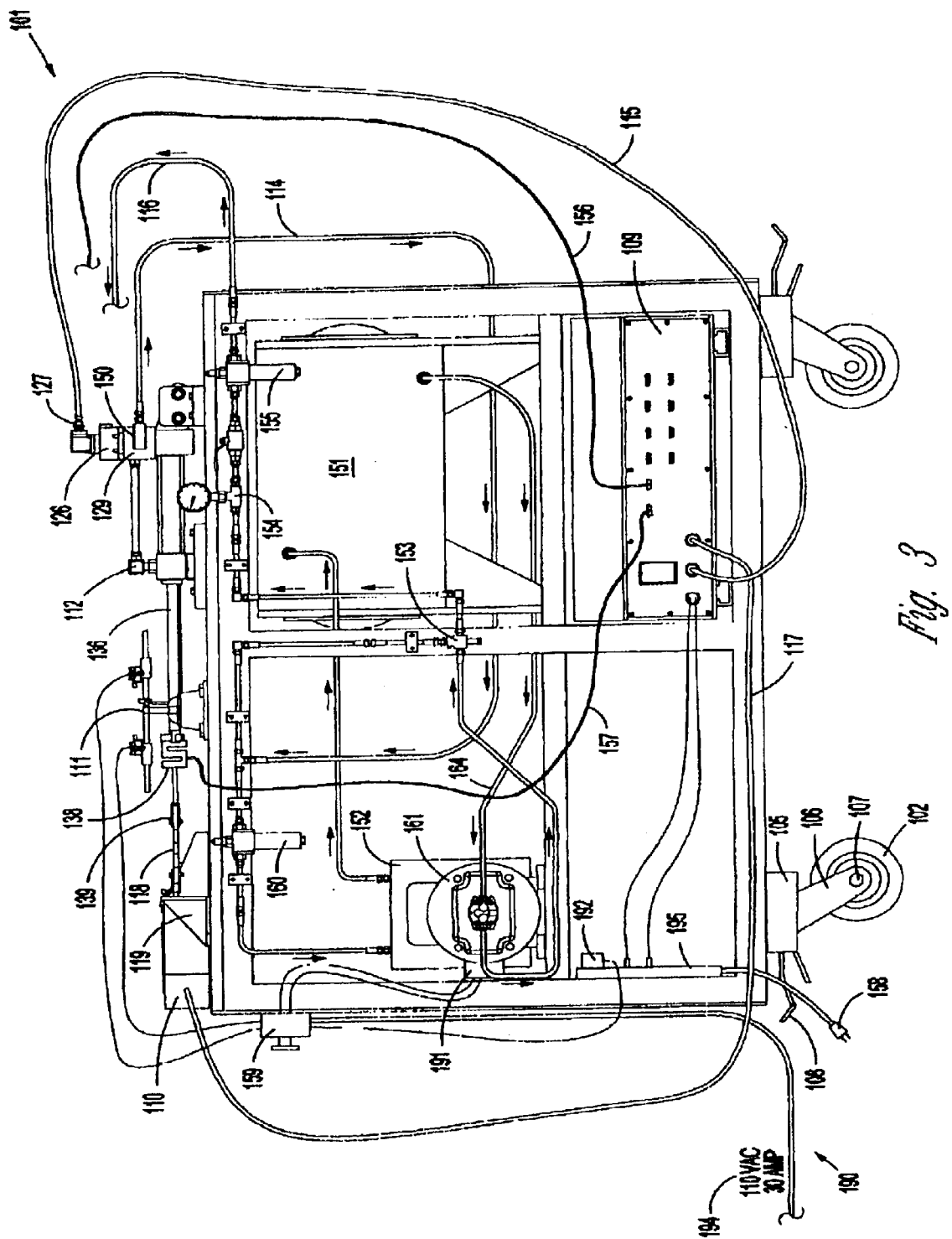
FIG. 3 is a front cross-sectional view of the preferred embodiment of the present invention.

In FIG. 3 a front cross-sectional view of the preferred embodiment of the present invention is shown. Test bench 101 having wheels 102 mounted to the bottom of test bench 101 by way of support brackets 105 is provided. Support brackets 105 connect to forks 106 on opposing sides of each wheel 102. Forks 106 connect to wheel 102 by way of hub 107. Locking means 108 is shown.

Control interface case 109 is provided and serves as the power interface for test bench 101. At control interface case 109, 0–10 volt DC fixed power source 109a (See FIG. 1) is provided as well as a 24 volt DC regulated power source 109b (See FIG. 1). A proportional integral derivative (PID) module 109c (See FIG. 1) is incorporated to regulate various process parameters such as pressure, total mass flow rate, phase volumetric fraction, phase mass flow rate, and pressure and liquid level. The regulation by the PID module 109c (See FIG. 1) is accomplished by controlling outlet pressure, inlet total mass flow rate, valve opening and pump velocity. Control interface case 109 also provides a ramp module 109d (See FIG. 1). Ramp module 109d (See FIG. 1) produces a DC output signal over an adjustable time rate setting based on the closure of an external contact. Ramp module 109d (See FIG. 1) can have integral LED's indicating that its output is at minimum, or has reached a maximum output state. Ramp module 109d (See FIG. 1) is useful for establishing a rate in which to achieve a pre-established setpoint or output state.

On top of test bench 101 is control station 110, displacement interlock control 11, and hydraulic ram 112. Control station 110 contains actuator knobs 121 (See FIG. 2) used in controlling the hydraulic ram 112 of the present invention. Control station 110 is connected to test bench 101 through a tethered cable 117 which connects to control interface case 109, more particularly ramp module 109d (See FIG. 4).

Hydraulic manifold 129 is provided on hydraulic ram 112. Pressure line 116 carries fluid from oil reserve 151 to the hydraulic manifold 129 of hydraulic ram 112. Initially hydraulic fluid travels from oil reserve 151 into line 164 through hydraulic pump 161 where it is pressurized. The preferred specifications for the hydraulic pump 161 are included in Table 3. A thermostat (not shown) is provided on oil reservoir 151 to visually monitor the temperature. Pressurized hydraulic fluid then enters pressure line 116 and goes through relief valve 153, pressure gauge 154, and oil filter 155 before entering hydraulic manifold 129 by way of union 131 (See FIG. 2). Return line 114 carries exhaust fluid from the hydraulic manifold 129 of hydraulic ram 112 back to the oil reserve 151 after passing through oil filter 160 and heat exchanger 152. On top of hydraulic manifold 129 is valve 126. Servo cable 115 is connected to valve 126 by way of coil (not shown) under housing 127. The opposite end of servo cable 115 is connected to control interface case 109, more particularly PID module 109c (See FIG. 4).

TABLE 3

Preferred Specifications for Hydraulic Pump 161.

| | |
|---|---|
| Operating Pressure | 3000 psi |
| Filtration | 3 micron or less |
| Recommended Temperature Range | 40 F. to 180 F. |
| Power | 110 VAC 30 AMP |

Displacement transducer 113 (See FIG. 1) is provided to measure hydraulic ram 112 stroke. A displacement transducer cable 156 connects displacement transducer 113 to control interface case 109, more specifically PID module 109c (See FIG. 4).

On one end of the hydraulic ram 112 is rod 136. A load/force cell 138, preferably an S-beam, is provided. Load/force cell 138 measures the load provided by hydraulic ram 112. A load/force cell transducer cable 157 connects load/force cell 138 to control interface case 109, more particularly, PID module 109c (See FIG. 4). On the opposite side of load/force cell 138 are two strain inducers 139 with a centrally connected test specimen 118. Connected at the opposite end of the second strain inducer 139 is reaction mount 119. Reaction mount 119 mounts to test bench 101.

A 110 VAC 30 amp circuit 194 provides power to master switch 159 via line 190. Master switch 159 provides power to hydraulic pump motor 191. A standard voltage 110 VAC plug 158 is provided for electrically connecting test bench 101 to a standard outlet (not shown). Power from 110 VAC plug 158 is provided to panel 195 which directs power to control interface case 109 and 24 volt transformer 192. Transformer 192 feeds power into relay (not shown) in master switch 159. Power from this transformer 192 is ultimately used to provide power to displacement interlock control 111.

Figure 4:
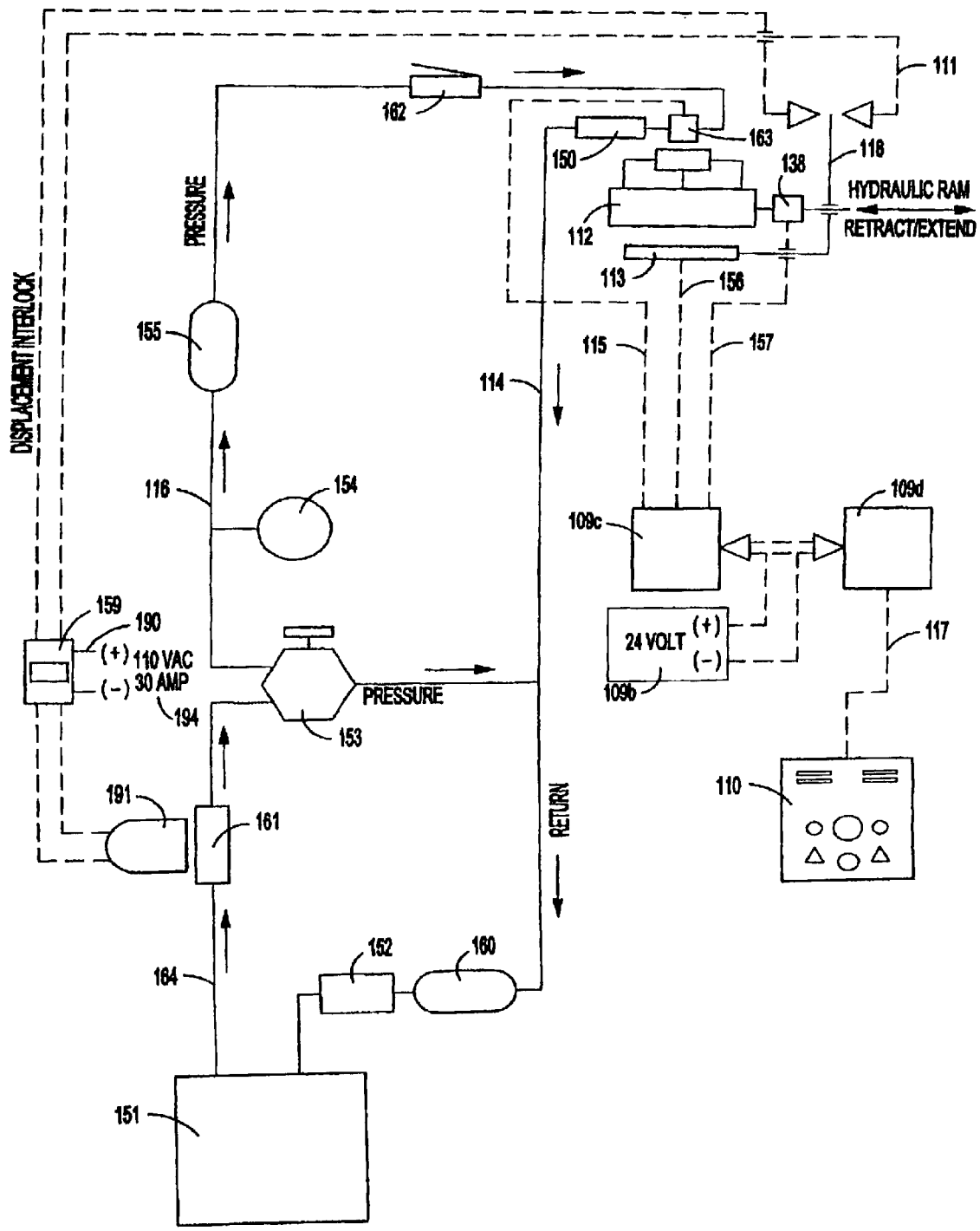
FIG. 4 is a schematic of the hydraulic and electrical assembly of the preferred embodiment of the present invention.

FIG. 4 is a schematic of the hydraulic and electrical assembly of the preferred embodiment of the present invention. The operation of the present schematic takes place on test bench 101 (See FIG. 1). Test bench 101 (See FIG. 1) has hydraulic pump 161 and oil reserve 151. Hydraulic fluid flows from oil reserve 151 into line 164 and into hydraulic pump 161. Hydraulic fluid then passes through hydraulic pump 161 and enters pressure line 116. The pressurized hydraulic fluid then flows through relief valve 153, oil filter 155 and ball valve 162 to a servo control valve 163. Servo control valve 163 controls the action of hydraulic ram 112. The preferred specifications for the servo control valve 163 are found in Table 4. Any return hydraulic fluid flows into return line 114 through check valve 150, oil filter 160, and heat exchanger 152 back to oil reserve 151. Relief valve 153 can pass relieved fluid into return line 114 for return to oil reserve 151.

TABLE 4

Preferred Specifications for Servo Control Valve 163.

| | |
|---|---|
| Rated Flow @1000 psi | 3.78–151 LPM (1.0–4.0 GPM) |
| Linearity | ≦5% |
| Hysteresis | ≦5% |
| Threshold | ≦5% |
| Operating Temperature | 30 to 225 F. |
| Pressure Gain | 3% of spool shift |
| Null Shift | With temp. ≦±2% per 100 F. |
| | With supply press <2% per 1000 psi |
| Quiescent Flow | 1.5–2.1 LPM (.40–.55 GPM) |

Servo control valve 163 with hydraulic ram 112 can be moved to the location where a test is to be performed. A displacement transducer 113 is included to determine how much a test item displaced. In addition, load/force cell 138 is provided to determine the load that is exerted on a test item.

PID module 109c operates displacement transducer 113 and load/force cell 138. A valve driver card (not shown) is provided within PID control module 109c which operates servo control valve 163. PID module 109c connects to servo control valve 163 by way of servo cable 115, to displacement transducer by way of displacement transducer cable 156, and to load/force cell 138 by way of load/force cell transducer cable 157. A ramp card (not shown) is provided within ramp module 109d which is responsible for receiving feedback signals from displacement transducer 113 and load/force cell 138. Ramp module 109d connects to control station 110 by way of tethered cable 117. A 24 volt DC regulated power source 109b provides power to PID module 109c and ramp module 109d.

A 110 VAC 30 amp circuit 194 provides power to master switch 159 via line 190. Master switch 159 provides power to hydraulic pump motor 191. A relay (not shown) within master switch 159 provides power to displacement interlock control 111.

Figure 5:
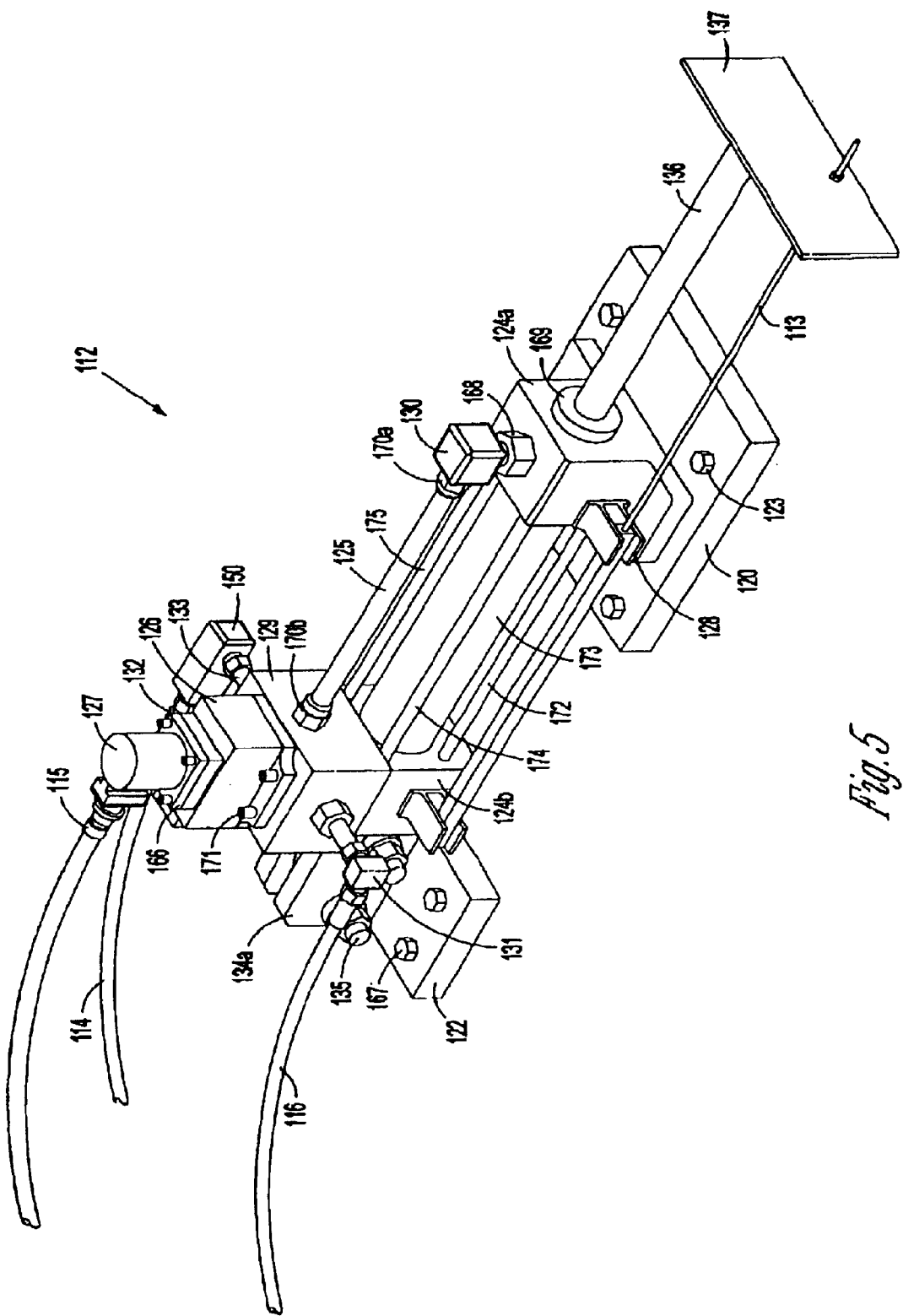
FIG. 5 is a close up view of the hydraulic ram of the preferred embodiment of the present invention.

In FIG. 5 a close up view of the hydraulic ram of the preferred embodiment of the present invention is shown. Hydraulic ram 112 is connected to the top of level plate 120 at one end of hydraulic ram 112 by way of hydraulic ram rod end cover 124a. The opposite end of hydraulic ram 112 is directly connected to test bench 101 (See FIG. 1) by way of hydraulic ram head end cover 124b. Hydraulic ram rod end cover 124a and hydraulic ram head end cover 124b are connected by way of ram member 173 and rods 125, 172, 174 and 175. Tube 125 is connected to hydraulic manifold 129 and hydraulic ram rod end cover 124a by way of nuts 170a and 170b. Nut 170b connects directly to hydraulic manifold 129 and nut 170a connects to union 130 on nut 168 of hydraulic ram rod end cover 124a. Positioned on top of hydraulic ram head end cover 124b is hydraulic manifold 129. Pressure line 116 carries fluid from hydraulic pump 161 (See FIG. 3) to the hydraulic manifold 129 of hydraulic ram 112 by way of union 131. Return line 114 carries exhaust fluid from the hydraulic manifold 129 of hydraulic ram 112 back to the oil reserve 151 (See FIG. 3) by way of union 133, check valve 150 and union 132. On top of hydraulic manifold 129 is valve 126 connected by way of mount 171. Servo cable 115 is connected to valve 126 by way of coil (not shown) under housing 127 and mount 166. Level plate 120 may or may not be attached to top 101a of test bench 101 by way of screws 123.

Connected by way of displacement transducer mounts 128 at the side of hydraulic ram 112 is displacement transducer 113. Base mount 122 is located adjacent hydraulic ram head end cover 124b. Base mount 122 connects to test bench 101 by way of screws 167 and connects to hydraulic ram head end cover 124b by way of mated arms 134 (See FIG. 1). Mated arms 134 (See FIG. 1) include two stationary arms 134a and one movable arm 134b (See FIG. 1). Stationary arms 134a and movable arm 134b (See FIG. 1) are connected by way of screws 135.

Extending on the opposite side of hydraulic ram rod end cover 124a portion of the hydraulic ram 112 is rod 136. Rod 136 connects to hydraulic ram rod end cover 124a by way of dowel 169. The opposite end of rod 136 connects to one face of plate 137.

Figure 6:
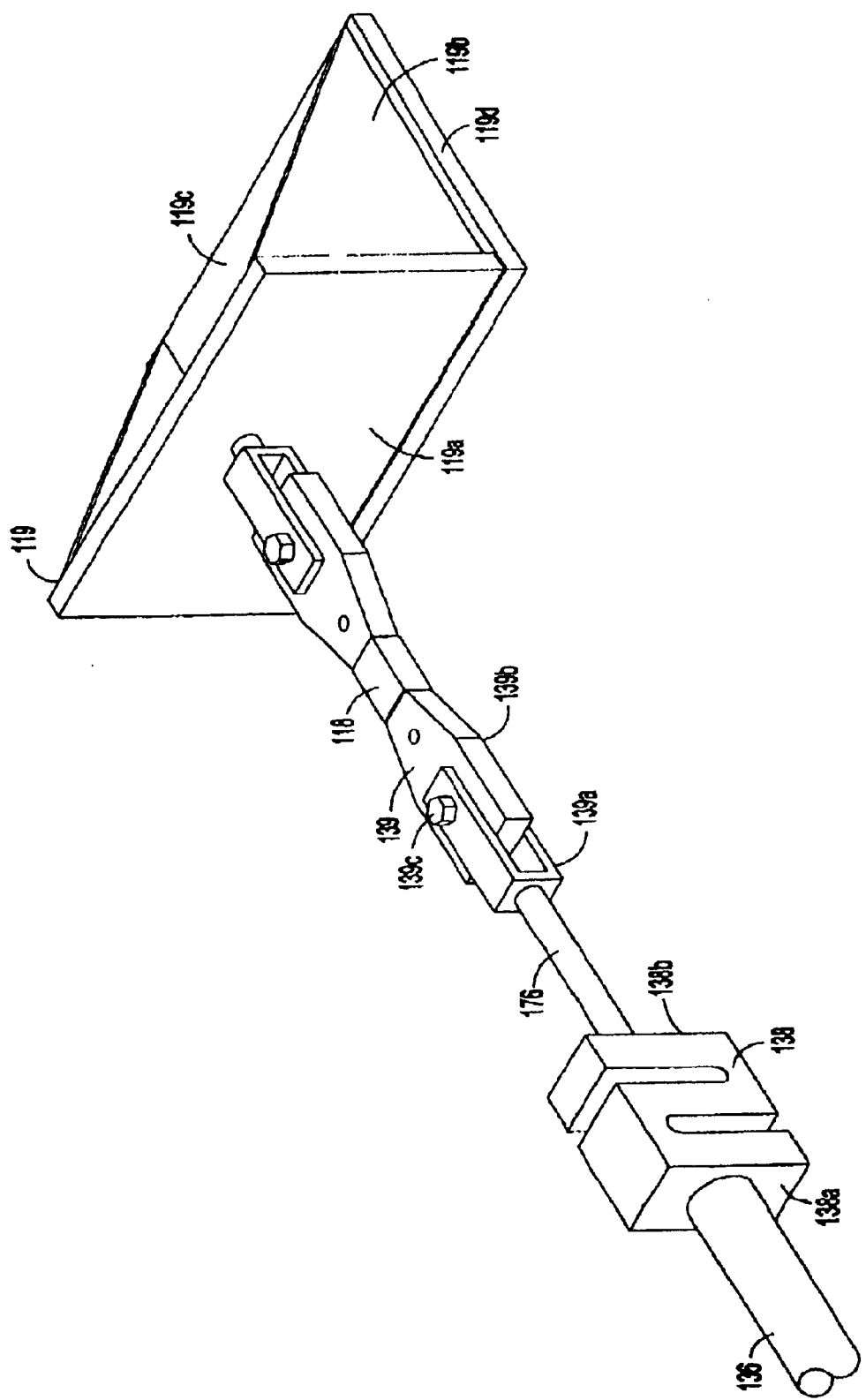
FIG. 6 is a close up view of the strain assembly which can be used with the preferred embodiment of the present invention.

FIG. 6 is a close up view of the strain assembly which can be used with the preferred embodiment of the present invention. This strain assembly is only required to assist in the understanding of the preferred embodiment, but is not required to operate the present invention. Rod 136 connects to one side 138a of load/force cell 138. Load/force cell 138 is preferably an S-beam. On the opposite side 138b of load/force cell 138 is strain connecting member 176. Strain connecting member 176 connects to one strain inducer 139. Strain inducer 139 is composed of a u-shaped member 139a and a flat member 139b. Flat member 139b fits partially within the u-portion of u-shaped member 139a at one end of flat member 139b and is secured to u-shaped member 139a by way of screw 139c. The other end of flat member 139b is connected to test specimen 118. A second strain inducer 139 oriented the opposite direction is connected to the opposing side of test specimen 118. Second strain inducer 139 is connected to reaction mount 119. Reaction mount 119 has a back 119a, side 119b, cavity 119c and bottom 119d. Bottom 119d of reaction mount 119 attaches to test bench 101 (See FIG. 1).

Figure 7:
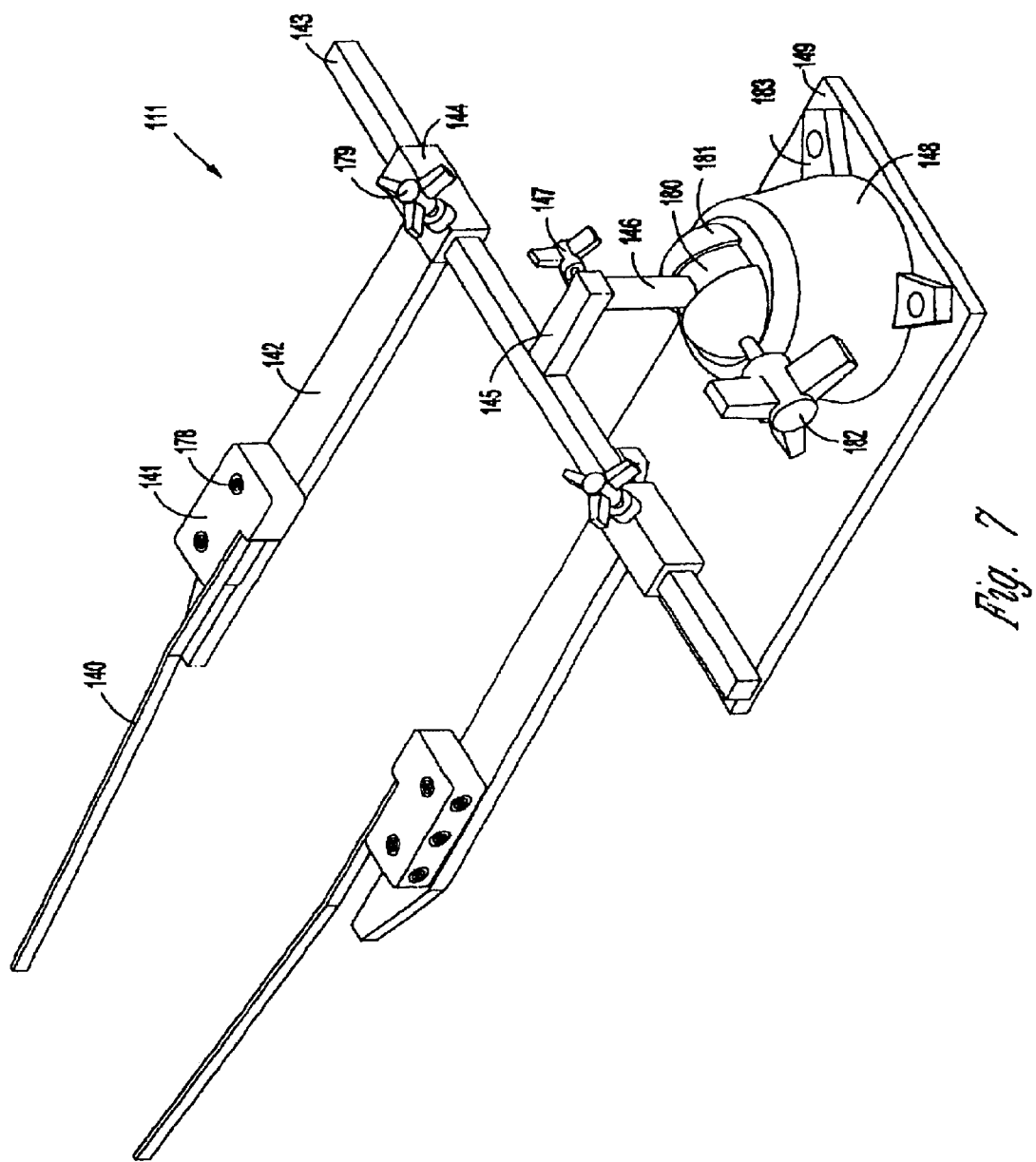
FIG. 7 is a close up view of the displacement interlock control of the preferred embodiment of the present invention.

In FIG. 7 a close up view of the displacement interlock control of the preferred embodiment of the present invention is shown. Situated above plate 137 (See FIG. 5) and load/force cell 138 (See FIG. 6) are arms 140 of displacement interlock control 111. At the opposite end of arms 140 are interlocks 141. Interlocks 141 are situated on bars 142 connected by way of connectors 178. Bars 142 end in a central member 143. A means for adjusting bars 144 is provided having wing nuts 179 for ease of tightening and loosening the connection of bars 142 to central member 143 and to allow the movement of bars 142 along central member 143. Central member 143 connects at the side of its length to side member 145. Side member 145 connects to post 146. An adjustment means 147 is provided between side member 145 and post 146 to allow the adjustment of post 146 in relation to side member 145. Adjustment means 147 is preferably a wing nut. Post 146 connects into pivot means 180 which allows pivotal vertical movement of post 146 in relation to base member 148. Rotation means 181 is provided surrounding pivot means 180 which allows rotation of post 146 in a horizontal plane in relation to base member 148. Locking means 182 is connected to rotation means 181 and allows locking of movement of pivot means 180 and rotation means 181 after movement. Base member 148 having feet 183 anchors displacement interlock control 111 to test bench 101(See FIG. 1) by way of platform 149.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A portable electro-hydraulic test bed apparatus comprising:
    a portable test bench incorporating an analog closed loop control system;
    a power interface associated with said test bench;
    a hydraulic ram situated upon said test bench, wherein said hydraulic ram incorporates a hydraulic manifold;
    a hydraulic pump associated with said hydraulic ram;
    an oil reserve for providing fluid to said hydraulic ram;
    a displacement transducer attached to said hydraulic ram;
    a load/force cell adjacent said hydraulic ram;
    a displacement interlock control adjacent said load/force cell;
    a control station associated with said test bench; and
    a pressure line connected to said hydraulic manifold.

2. The portable electro-hydraulic test bed apparatus of claim 1 further comprising a relief valve connected along said pressure line.

3. The portable electro-hydraulic test bed apparatus of claim 2 further comprising a return line connected to said hydraulic manifold.

4. The portable electro-hydraulic test bed apparatus of claim 3 further comprising a heat exchanger along said return line.

5. The portable electro-hydraulic test bed apparatus of claim 4 further comprising a ball valve along said pressure line.

6. The portable electro-hydraulic test bed apparatus of claim 5 further comprising a servo control valve associated with said hydraulic ram.

7. The portable electro-hydraulic test bed apparatus of claim 6 wherein said PID module is connected to said servo control valve by way of a servo control cable.

8. The portable electro-hydraulic test bed apparatus of claim 7 wherein said PID module is connected to said displacement transducer by way of a displacement transducer cable.

9. The portable electro-hydraulic test bed apparatus of claim 8 wherein said PID module is connected to said load/force cell by way of a load/force cell cable.

10. The portable electro-hydraulic test bed apparatus of claim 9 wherein said power interface includes a fixed power source, regulated power source, PID module, and ramp module.

11. A method of operating a portable electro-hydraulic test bed apparatus comprising the steps of:

providing a portable test bench with a power interface having a hydraulic ram situated upon said portable test bench adjacent a load/force cell and displacement interlock control and incorporating an analog closed loop control system;

attaching a test item to said portable test bench;

activating a hydraulic pump associated with said hydraulic ram;

pumping fluid from an oil reserve to said hydraulic ram;

displacing said test item to activate a displacement transducer attached to said hydraulic ram;

applying a force to said test item to activate a load/force cell adjacent said hydraulic ram; and controlling said displacing step and said applying step with an analog control station.

12. The method of operating a portable electro-hydraulic test bed apparatus of claim 11 wherein said power interface includes a fixed power source, regulated power source, PID module, and ramp module.

13. The method of operating a portable electro-hydraulic test bed apparatus of claim 12 wherein said hydraulic ram incorporates a hydraulic manifold.

14. The method of operating a portable electro-hydraulic test bed apparatus of claim 13 further comprising the step of providing a pressure line connected to said hydraulic manifold for supplying fluid to said hydraulic manifold.

15. The method of operating a portable electro-hydraulic test bed apparatus of claim 14 further comprising the step of providing a relief valve connected along said pressure line for releasing pressure along said pressure line.

16. The method of operating a portable electro-hydraulic test bed apparatus of claim 15 further comprising the step of providing a return line connected to said hydraulic manifold for returning fluid to said oil reserve.

* * * * *